United States Patent
Otsuki et al.

(10) Patent No.: US 9,140,631 B2
(45) Date of Patent: Sep. 22, 2015

(54) METHOD OF MEASURING CHARACTERISTICS OF CRITICAL ORIFICE TYPE CONSTANT FLOW RATE INSTRUMENT FOR USE IN MULTISTAGE DILUTION MECHANISM

(75) Inventors: Yoshinori Otsuki, Kyoto (JP); Masayoshi Shinohara, Kyoto (JP); Kazuo Hanada, Kyoto (JP)

(73) Assignee: HORIBA, LTD., Kyoto (JP)

( * ) Notice: Subject to any disclaimer, the term of this patent is extended or adjusted under 35 U.S.C. 154(b) by 768 days.

(21) Appl. No.: 13/348,826

(22) Filed: Jan. 12, 2012

(65) Prior Publication Data

US 2012/0174989 A1 Jul. 12, 2012

(30) Foreign Application Priority Data

Jan. 12, 2011 (JP) ................................. 2011-003867

(51) Int. Cl.
*G01N 1/22* (2006.01)
*G01N 33/00* (2006.01)
*G01N 15/06* (2006.01)

(52) U.S. Cl.
CPC ............ *G01N 1/2252* (2013.01); *G01N 1/2202* (2013.01); *G01N 15/065* (2013.01); *G01N 33/005* (2013.01); *G01N 2001/2264* (2013.01); *Y10T 137/2499* (2015.04)

(58) Field of Classification Search
CPC .................... G01N 1/2252; G01N 2001/2264; G01N 1/22; G01N 2015/0046
USPC ........................................................ 73/23.31
See application file for complete search history.

(56) References Cited

U.S. PATENT DOCUMENTS

2006/0076060 A1 4/2006 Ohmi et al.

FOREIGN PATENT DOCUMENTS

| CN | 1739072 A | 2/2006 |
|---|---|---|
| EP | 1884761 A1 | 2/2008 |
| EP | 2006005 A9 | 12/2008 |
| JP | 2000-028499 | 1/2000 |
| JP | 2006194726 A | 7/2006 |
| JP | 2008164446 A | 7/2008 |
| JP | 2010-249754 | 11/2010 |

(Continued)

OTHER PUBLICATIONS

English Language translation of the Description from JP2008/164446. Translated on Oct. 1, 2014 from <http://worldwide.espacenet.com/>.*

(Continued)

*Primary Examiner* — Lisa Caputo
*Assistant Examiner* — Punam Roy
(74) *Attorney, Agent, or Firm* — Brooks Kushman P.C.

(57) ABSTRACT

A method of measuring characteristics of a critical orifice type constant flow rate instrument is applied to a dilution mechanism including dilution units in series. Diluent gas of one dilution unit and diluent gas of the other dilution unit are kept flowing in a derivation flow passage for deriving redundant gas of the corresponding one dilution unit in a manner that the total flow rate thereof is equal to a prescribed constant flow rate and that the flow rate of the diluent gas from the corresponding dilution unit is equal to the flow rate in use. The flow rate characteristics of the critical orifice type constant flow rate instrument are measured based on at least an upstream side pressure of the critical orifice type constant flow rate instrument provided in the derivation flow passage at this time.

10 Claims, 7 Drawing Sheets

(56) References Cited

FOREIGN PATENT DOCUMENTS

JP    2010-261938    11/2010

OTHER PUBLICATIONS

Office Action dated Feb. 10, 2015 issued for Japanese patent application No. 2011-286665, 3 pgs.

Office Action dated Apr. 21, 2015 issued for Chinese patent application No. 201210007970.5, 5 pgs.

Kang Jianzhen et al, A Novel Interface for Coupling Capillary Electrophoresis with Inductively Coupled Plasma Mass Spectrometry, Chinese Journal of Analytical Chemistry, vol. 32(2), Feb. 2004, pp. 262-266.

* cited by examiner

METHOD OF MEASURING CHARACTERISTICS OF CRITICAL ORIFICE TYPE CONSTANT FLOW RATE INSTRUMENT FOR USE IN MULTISTAGE DILUTION MECHANISM

CROSS-REFERENCE TO RELATED APPLICATION

This application claims priority to Japanese Patent Application No. 2011-003867 filed Jan. 12, 2011, the disclosure of which is incorporated in its entirety by reference herein.

TECHNICAL FIELD

The present invention relates to a gas analyzing system analyzing such as, e.g., particulate matters, a multistage dilution mechanism appropriately used therein and a method of measuring characteristics of a critical orifice type constant flow rate instrument for use in the multistage dilution mechanism.

BACKGROUND ART

Particulate matters (PM), i.e., one sort of exhaust substances of an internal combustion engine is reduced to be minute in amount by improvement in performance of the engine, and it becomes difficult in situation to measure the same by a conventional filter-type weighing method. Therefore, as an alternative of the filter-type weighing method, there has been developed a technique of measuring the number of PM contained in exhaust gas. As a specific system configuration thereof, there has been known a technique such that, for example, a dilution unit for diluting exhaust gas of an internal combustion engine with air etc. is provided in a front stage of a particle number measuring device so that a part of the diluted exhaust gas is led to the particle number measuring device so as to count the number of the particles contained therein (see Patent Literature 1).

The dilution unit has a basic structure such that a diluent gas flow passage is connected to an intermediate portion of a main flow passage communicating between an input terminal and an output terminal so that diluent gas is mixed with the input gas introduced through the input terminal so that the resultant mixed gas is outputted through the output terminal.

By the way, in the case where a dilution ratio is desired to be increased, although the dilution units as mentioned above are connected in series, if the dilution units are simply connected, the flow rate of the input gas to a subsequent dilution unit becomes too large to dilute the inflow gas. Therefore, as disclosed in Patent Literature 2, some or whole of the dilution units are provided with derivation flow passages branched from the respective main flow passages for deriving a part of the gas flowing inside thereof so that the flow rate of the output gas is reduced.

Therefore, each of the derivation flow passages is provided with, e.g., a critical orifice type constant flow rate instrument so that the flow rate of the derivation flow passage is made constant so as to be measured. It is noted that, the critical orifice type constant flow rate instrument is intended to have a construction such that an upstream side pressure thereof is made higher than the downstream side pressure over a prescribed ratio so that a flow velocity at a throttle portion becomes the sonic velocity. The flow rate Q thereof becomes depending only on the upstream side pressure $P_1$ and temperature T but independent of the downstream side pressure as shown by following Formula (A):

$$Q = 600 \cdot C \cdot (P_1 + 0.1) \cdot (293/T)^{1/2} \qquad (A)$$

Therefore, if the upstream side pressure and temperature are kept constant without being affected by a pulsation etc. of a suction pump, a constant flow rate can be obtained. Meanwhile, upon measurement of the upstream side pressure and temperature, the flow rate at that time can be calculated. Also, in the critical orifice type constant flow rate instrument like this, it is necessary to measure the flow rate characteristics, for example, determine C (sonic conductance) prior to use. In specific, a known flow rate is rendered to flow and the pressure and temperature at that time are measured so as to calculate C based on the measured values (this process also referred to as "calibration" hereinafter).

Thus, in the case of a gas analyzing system of this type, when the critical orifice type constant flow rate instrument is calibrated, diluent gas of a prescribed flow rate controlled by flow rate control means is led from a diluent gas flow passage of the dilution unit to the critical orifice type constant flow rate instrument so as to measure the upstream side pressure and temperature at this time. The prescribed flow rate is a flow rate that is set to the critical orifice type constant flow rate instrument in actual use.

CITATION LIST

Patent Literature

Patent Literature 1: JP2006-194726A
Patent Literature 2: JP2008-164446A

SUMMARY OF INVENTION

Technical Problem

In the dilution unit in actual use, however, since the input gas in addition to the diluent gas is introduced and these gases are mixed and flow into the derivation flow passage, i.e., critical orifice type constant flow rate instrument, the flow rate conditions are very different in calibration and in actual use, which may not be a proper calibration.

For example, when in calibration time and when in actual use, the flow rates of the diluent gas controlled by the flow rate control means of the corresponding dilution unit are different. In other words, when used, since a part of the input gas also flows into the critical orifice type constant flow rate instrument, the flow rate of the diluent gas becomes a smaller value than in the calibration time.

Then, as shown in FIG. 1, if there is an error in flow rate linearity characteristics of the flow rate control means, the error component appears as a flow rate error of the critical orifice type constant flow rate instrument, which in turn becomes an error of a dilution ratio. When counting PM, an extremely accurate measurement is recently demanded as mentioned above and therefore the error of the dilution ratio is undesirable.

Moreover, for example, in the case where the input gas is heated to be a high temperature at an intermediate portion of a pipe in usage, if only the diluent gas of the corresponding dilution unit is simply poured into the critical orifice type constant flow rate instrument so as to perform the calibration as is conventionally performed, the gas temperature becomes different from that when in usage, which may result in insufficient calibration.

The present invention has been made to solve the problems mentioned above, and an essential object thereof is to bring the condition at the time of measuring the characteristics of the critical orifice type constant flow rate instrument near to the condition in actual use as close as possible by using diluent gas of the other dilution unit so as to reduce the error of the dilution ratio.

Solution to Problem

That is, a method of measuring characteristics of a critical orifice type constant flow rate instrument pertaining to the invention of a first aspect is applied to a dilution mechanism constructed in a manner that, each of a plurality of dilution units is constructed such that a confluence is provided at an intermediate portion of a main flow passage connecting between an input terminal and an output terminal for leading input gas and a diluent gas flow passage provided with flow rate control means is connected to the confluence so that diluent gas of a prescribed flow rate to have a predetermined dilution ratio is introduced to the main flow passage and the plurality of dilution units are connected in series and a part or whole of the dilution units is provided with a branch point at the intermediate portion of the main flow passage so that a derivation flow passage provided with the critical orifice type constant flow rate instrument is connected to the branch point so as to derive the gas of a constant flow rate from the main flow passage.

Herein, to a derivation flow passage of one of the dilution units, the diluent gas from the diluent gas flow passage in the corresponding one dilution unit and the diluent gas from the diluent gas flow passages in one or more other dilution units are kept flowing in a manner that the total flow rate thereof is equal to the constant flow rate and that the flow rate of the diluent gas from the corresponding one dilution unit is equal to the prescribed flow rate, whereby the flow rate characteristics of the corresponding critical orifice type constant flow rate instrument are measured based on at least an upstream side pressure of the critical orifice type constant flow rate instrument in the corresponding derivation flow passage at this time.

With this arrangement, when performing a calibration, since the diluent gas for the corresponding one dilution unit is rendered to flow by a flow rate equal to that in use with the diluent inflow gas from the other dilution unit used as simulation input gas so that the operating points of the flow rate control means regarding the diluent gas both in use and in calibration are made coincident with each other, the error mentioned above can be reduced. This aspect is particularly effective in the case of frequently performing the calibrations compared to the invention of a second aspect of the present invention to be described later.

A method of measuring characteristics of a critical orifice type constant flow rate instrument according to the second aspect of the present invention is applied to a dilution mechanism similarly to the first aspect of the present invention. Herein, to a derivation flow passage of one of the dilution units, the diluent gas from the diluent gas flow passage in the corresponding one dilution unit and the diluent gas from the diluent gas flow passages in one or more other dilution units are kept flowing in a manner that the total flow rate thereof is equal to the constant flow rate and that a dilution ratio of the flow rate of the diluent gas from the one or more other dilution units to the flow rate of the diluent gas from the corresponding one dilution unit is equal to the predetermined dilution ratio, whereby the flow rate characteristics of the corresponding critical orifice type constant flow rate instrument are measured based on at least an upstream side pressure of the critical orifice type constant flow rate instrument in the corresponding derivation flow passage at this time.

Even with this arrangement, since the conditions in use and in calibration are brought nearer compared to the conventional arrangement, there can be obtained an effect similar to that in the first aspect of the present invention. Moreover, this aspect is particularly effective in the case of frequently changing the dilution ratio, compared to the invention of the first aspect of the present invention.

A third aspect of the present invention is characterized in that the other dilution unit is an upstream side or downstream side dilution unit adjacent to the corresponding one dilution unit. With this arrangement, since the passage of the input gas can be made closer to the condition in use, the temperature can be easily adjusted equally both in use and in calibration to be more desirable.

A dilution mechanism pertaining to the invention of a fourth aspect is constructed in a manner that, each of a plurality of dilution units is constructed such that a confluence is provided at an intermediate portion of a main flow passage connecting between an input terminal and an output terminal for leading input gas and a diluent gas flow passage provided with flow rate control means is connected to the confluence so that diluent gas of a prescribed flow rate to have a predetermined dilution ratio is introduced to the main flow passage and the plurality of dilution units are connected in series and a part or whole of the dilution units is provided with a branch point at the intermediate portion of the main flow passage so that a derivation flow passage provided with the critical orifice type constant flow rate instrument is connected to the branch point so as to derive the gas of a constant flow rate from the main flow passage.

Herein, into a derivation flow passage of one of the dilution units, only the diluent gas from the diluent gas flow passage in the corresponding one dilution unit and the diluent gas from the diluent gas flow passages in one or more other dilution units are flowable, and the dilution mechanism includes an information processing device controlling the flow rate control means in a manner that the total flow rate of the respective diluent gas at this time is equal to the constant flow rate and that the flow rate of the diluent gas from the corresponding one dilution unit is equal to the prescribed flow rate and measuring the flow rate characteristics of the corresponding critical orifice type constant flow rate instrument based on at least an upstream side pressure of the critical orifice type constant flow rate instrument in the corresponding derivation flow passage. With this arrangement, there can be obtained an effect similar to that in the invention pertaining to the first aspect of the present invention.

A dilution mechanism pertaining to the invention of a fifth aspect is constructed in a manner that, each of a plurality of dilution units is constructed such that a confluence is provided at an intermediate portion of a main flow passage connecting between an input terminal and an output terminal for leading input gas and a diluent gas flow passage provided with flow rate control means is connected to the confluence so that diluent gas of a prescribed flow rate to have a predetermined dilution ratio is introduced to the main flow passage and the plurality of dilution units are connected in series and a part or whole of the dilution units is provided with a branch point at the intermediate portion of the main flow passage so that a derivation flow passage provided with the critical orifice type constant flow rate instrument is connected to the branch point so as to derive the gas of a constant flow rate from the main flow passage.

Herein, into a derivation flow passage of one of the dilution units, only the diluent gas from the diluent gas flow passage in the corresponding one dilution unit and the diluent gas from the diluent gas flow passages in one or more other dilution units are flowable, and the dilution mechanism includes an information processing device controlling the flow rate control means in a manner that the total flow rate of the respective diluent gas at this time is equal to the constant flow rate and that the dilution ratio of the flow rate of the diluent gas from the one or more other dilution units to the flow rate of the diluent gas from the corresponding one dilution unit is equal to the predetermined dilution ratio and measuring the flow rate characteristics of the corresponding critical orifice type constant flow rate instrument based on at least an upstream side pressure of the critical orifice type constant flow rate instrument in the corresponding derivation flow passage. With this arrangement, there can be obtained an effect similar to that in the second aspect of the present invention.

A gas analyzing system according to a sixth aspect of the present invention includes the dilution mechanism according to the fifth aspect of the present invention and further includes ingredient analyzing means adapted to analyze ingredients of exhaust gas of an internal combustion engine introduced to a first-stage dilution unit and derived from a last-stage dilution unit. With this arrangement, the effect of the first aspect of the present invention and the like becomes remarkable.

A gas analyzing system according to a seventh aspect of the present invention is characterized in that the ingredient analyzing means includes critical orifice type constant flow rate means inside thereof and is constructed such that only the diluent gas from the dilution unit is flowable into the ingredient analyzing means by a prescribed flow rate, wherein the information processing device measures the flow rate characteristics of the ingredient analyzing means based on at least an upstream side pressure of the ingredient analyzing means at this time.

With this arrangement, also the flow rate characteristics of the ingredient analyzing means can be accurately measured.

More specifically, it is desirable that the ingredient analyzing means is a particulate matters counter counting the particulate matters contained in the exhaust gas.

Advantageous Effects of Invention

As described above, according to the present invention, even when measuring the flow rate characteristics (i.e., calibrating) of the critical orifice type constant flow rate instrument for use in a dilution unit, since the conditions (e.g., temperature, pressure and flow rate) substantially the same as those in use can be set up, the characteristics measurement accuracy can be remarkably improved and the accuracy of the dilution of the dilution unit can be increased. As a result, it becomes possible to improve the measurement accuracy of a gas analyzing system etc. using this kind of a dilution unit.

DESCRIPTION OF EMBODIMENTS

The following describes one embodiment of a gas analyzing system pertaining to the present invention with reference to the drawings.

Figure 1:
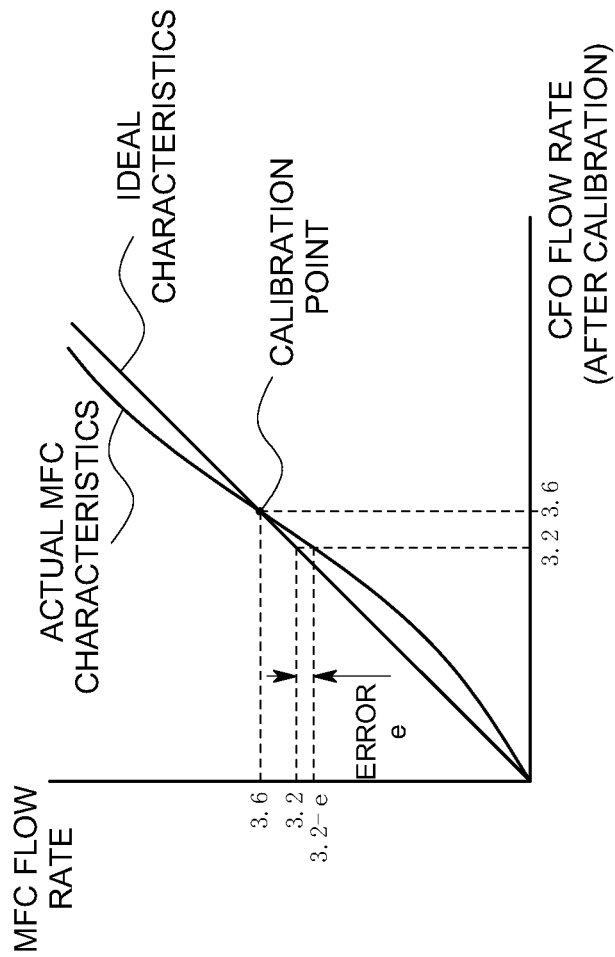
FIG. 1 is an explanatory diagram explaining a cause of an error.
Figure 2:
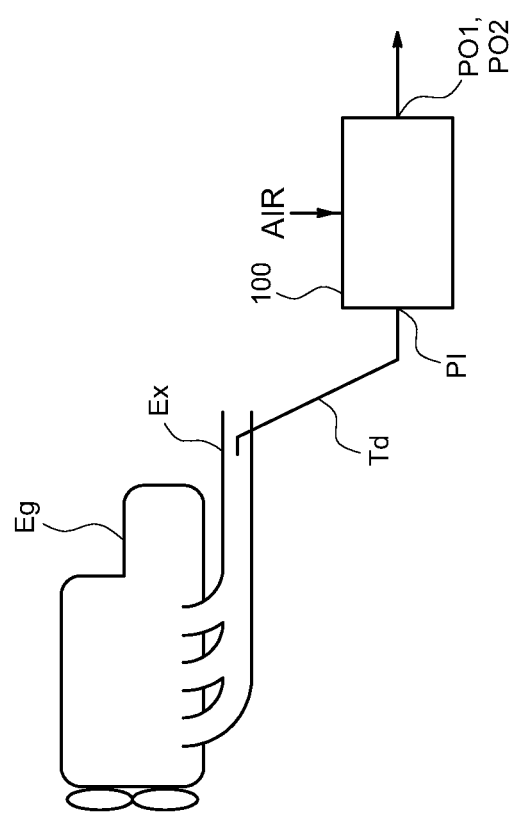
FIG. 2 is a schematic view showing an overall analyzing system in which a gas analyzing system pertaining to one embodiment of the present invention is connected to an internal combustion engine.

As shown in FIG. 2, the gas analyzing system 100 pertaining to the present embodiment is adapted to sample a part of exhaust gas which is a measurement gas through a branch flow passage Td branched from an exhaust pipe Ex of an internal combustion engine Eg so as to count the number of solid particles PM contained therein. It is noted here that the exhaust gas is a raw exhaust gas exhausted from the internal combustion engine but may be an exhaust gas diluted through, e.g., a full-flow dilution tunnel or branch flow dilution tunnel. That is, the exhaust gas in the present application means inclusion of the exhaust gas diluted as mentioned above in addition to the raw exhaust gas.

Next, the internal structure of the gas analyzing system 100 is described with reference to FIG. 3.

Figure 3:
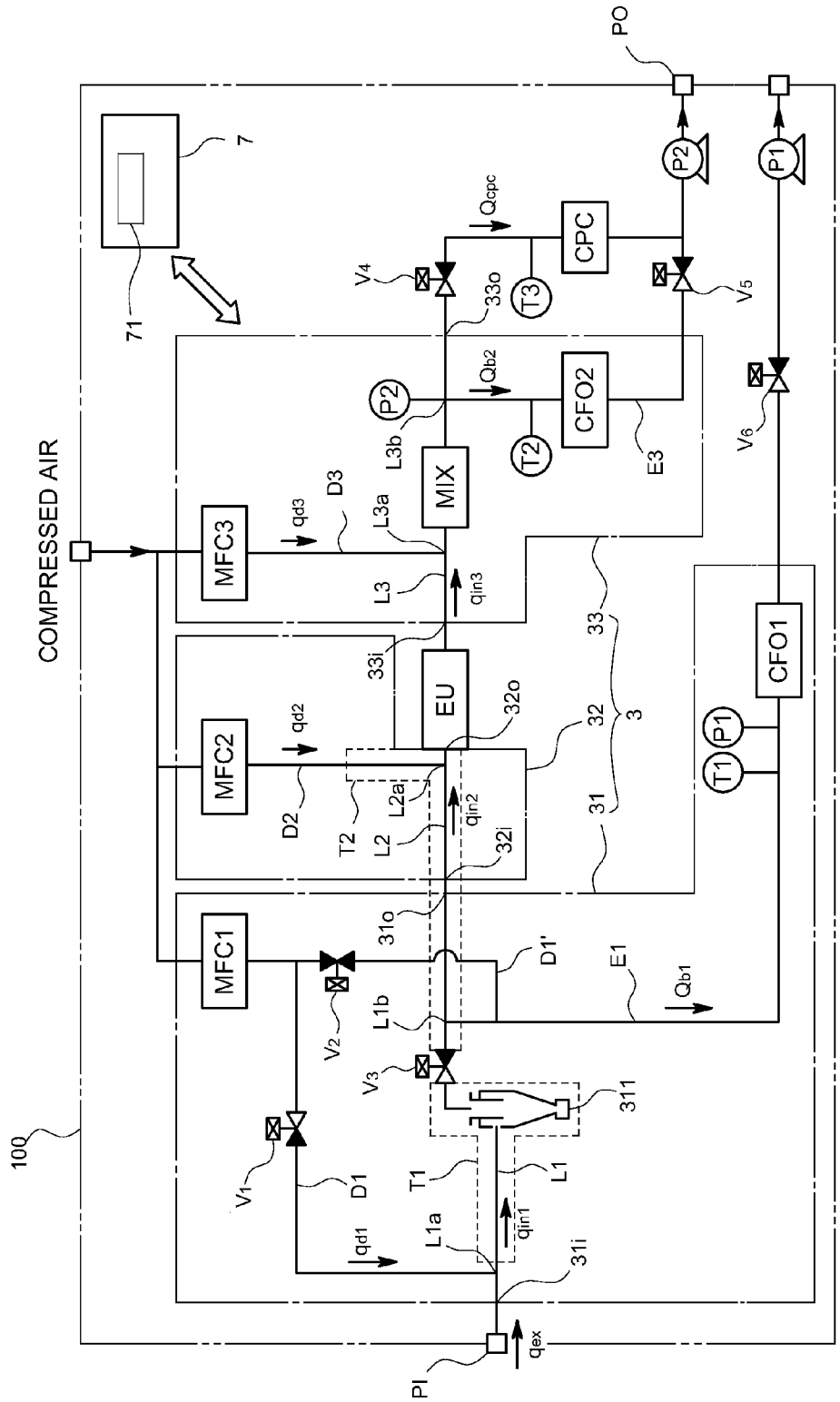
FIG. 3 is a fluid circuit diagram showing an internal structure of the gas analyzing system in the same embodiment and displaying a flow of the gas when in use thereof.

A reference symbol PI in FIG. 3 shows an exhaust gas introduction port. The exhaust gas of the internal combustion engine Eg is led from the branch flow passage Td to the inside through the exhaust gas introduction port PI. Then, the exhaust gas is diluted by a dilution mechanism 3 provided in the gas analyzing system and thereafter led to particulate matters counting means CPC that is one kind of ingredient analyzing means and connected to the subsequent stage thereof so that the number of PM contained inside thereof is counted.

Next, each of parts is explained.

The dilution mechanism 3 includes three-stage dilution units 31, 32 and 33 provided in series.

The dilution units 31, 32 and 33 are respectively provided with, as basic components, input terminals 31$i$, 32$i$ and 33$i$ introducing the input gas, output terminals 31$o$, 32$o$ and 33$o$ deriving the gas, main flow passages L1, L2 and L3 connected between the input terminals 31$i$, 32$i$ and 33$i$ and the output terminals 31$o$, 32$o$ and 33$o$, and diluent gas flow passages D1, D2 and D3 connected to confluences L1$a$, L2$a$ and L3$a$ provided at an intermediate portion of the main flow passages L1, L2 and L3. The diluent gas flow passages D1, D2 and D3 are respectively provided with flow rate control means (herein, mass flow controllers) MFC1, MFC2 and MFC3. The flow rates of inflow diluent gases are controlled by the flow rate control means MFC1, MFC2 and MFC3 so that the input gases are diluted at prescribed dilution ratios so as to output the mixed gas of the diluted gases.

In the first-stage dilution unit 31, the input terminal 31$i$ is connected to the exhaust gas introduction port PI and the output terminal 31$o$ thereof is connected to the input terminal 32$i$ of the middle-stage dilution unit 32. A branch point L1$b$ is provided in the downstream side than the confluence L1$a$ in the main flow passage L1 so that a derivation flow passage E1 is connected to the branch point L1$b$. A suction pump P1 is provided at a distal end of the derivation flow passage E1 and a critical orifice type constant flow rate instrument CFO1 is provided at the intermediate portion thereof so that a prescribed constant flow rate gas of the entire gas flowing in the main flow passage L1 is derived from the derivation flow passage E1 and the remaining gas is outputted from the output terminal 31o. Also, as described above, the critical orifice type constant flow rate instrument CFO1 is intended to have a construction such that an upstream side pressure thereof is made higher than the downstream side pressure over a prescribed ratio so that a flow velocity at a throttle portion becomes the sonic velocity while the flow rate thereof depends only on the upstream side pressure and temperature thereof but does not depend on the downstream side pressure.

It is noted that a reference numeral 311 depicted in the main flow passage L1 denotes dust removal means such as a cyclone. A flow passage D1' branched from the diluent gas flow passage D1 and connected to the derivation flow passage E1 is a bypass flow passage that is used in calibration to be described later. Moreover, the temperature from the exhaust gas introduction port PI to the dust removal means 311 is kept at a first temperature by a temperature controller T1 (herein, e.g., approximately 40 to 50 degree). Further, reference symbols V1 to V6 denote ON/OFF valves.

The middle-stage dilution unit 32 has the basic components mentioned before wherein the output terminal 32o thereof is connected to the last-stage dilution unit 33 through an evaporator unit EU. This dilution unit 32 is not provided with a derivation flow passage as in the first-stage dilution unit 31. The evaporator unit EU is provided here having a main object to remove volatile particles and is kept at a temperature of, e.g., about 300-400° C. Moreover, the main flow passages L1 and L2 in the first-stage and middle-stage dilution units 31 and 32 extending from the dust removal means 2 to the evaporator unit EU and the diluent gas flow passage D2 except the vicinity of the flow rate control means MFC1 in the middle-stage dilution unit 32 are kept at a second temperature by a temperature controller T2 (herein, e.g., about 150-250° C.). This is to prevent adhesion and agglomeration etc. of PM to an inner wall of the pipe so as to suppress the counting error.

The last-stage dilution unit 33 has a configuration that the input terminal 33i thereof is connected to an outlet of the evaporator unit EU and the output terminal 33o thereof is connected to the particulate matters counting means CPC. A branch point L3b is provided in the downstream side than the confluence L3a in the main flow passage L3 so that a derivation flow passage E3 is connected to the branch point L3b. A suction pump P2 is provided at a distal end of the derivation flow passage E3 and a critical orifice type constant flow rate instrument CFO2 is provided at the intermediate portion thereof so that a prescribed constant flow rate gas of the entire gas flowing in the main flow passage L3 is derived from the derivation flow passage E3 and the remaining gas is introduced to the particulate matters counting means CPC. Herein, the outlet of the particulate matters counting means CPC is connected to a distal end portion of the derivation flow passage E3 and the suction pump P2 is commonly used for the derivation flow passage 3 and the particulate matters counting means CPC.

Figure 4:
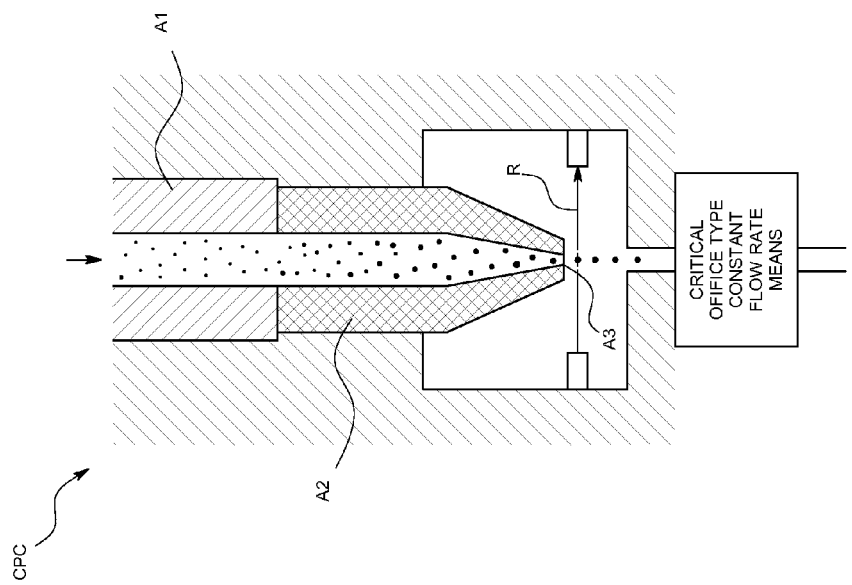
FIG. 4 is a schematic diagram schematically showing an internal structure of particulate matters counting means in the same embodiment.

As shown in FIG. 4, the particulate matters counting means CPC has a configuration that the introduced gas is lead a heating part A1 including an organic gas such as alcohol or butanol and is thereafter cooled in a condenser part A2 so that the organic gas is condensed to be adhered to the PM contained in the exhaust gas. Then, the PM is grown to have a large size in diameter and the grown PM is exhausted through a slit A3 so that the exhausted particles are counted with a laser beam R. Such the particulate matters counting means CPC configured as described above includes a critical orifice type constant flow rate means in the downstream so that a constant flow rate gas flows in the particulate matters counting means CPC.

Further, in this embodiment, there is provided an information processing device 7 for controlling the flow rate control means and the like. This information processing device is so-called a general-purpose or special-purpose computer including a CPU, a memory, input means, a display and the like to be operated in co-operation with the CPU and peripheral equipment in accordance with a predetermined program stored in the memory. In the present embodiment, the information processing device 7 is configured to act at least a function of a diluent gas control unit 71 in accordance with the program.

An operation of the gas analyzing system 100 configured as described above in use is described below.

First, assuming that valves V1, V3, V4, V5 and V6 are opened while a valve V2 is closed.

Herein, it is assumed that, a flow rate flowing through the constant flow rate instrument CFO1 is set to $Q_{b1}$, a flow rate flowing through the constant flow rate instrument CFO2 is set to $Q_{b2}$ and a flow rate flowing through the particulate matters counting means CPC is set to $Q_{CPC}$ and the dilution ratios (input gas flow rate/input gas flow rate+diluent gas flow rate) in the respective dilution units 31 to 33 are determined to be $R_{d1}$, $R_{d2}$ and $R_{d3}$, respectively.

Here, $R_{d1}$, $R_{d2}$ and $R_{d3}$ are represented by following formulae (1) to (3):

$$R_{d1} = q_{in1}/(q_{in1}+q_{d1}) \qquad (1)$$

$$R_{d2} = q_{in2}/(q_{in2}+q_{d2}) \qquad (2)$$

$$R_{d3} = q_{in3}/(q_{in3}+q_{d3}) \qquad (3)$$

Herein, $R_{d1}$, $R_{d2}$ and $R_{d3}$ respectively represent the dilution ratios in the first-stage dilution unit 31, the middle-stage dilution unit 32 and the last-stage dilution unit 33, $q_{in1}$, $q_{in2}$ and $q_{in3}$ respectively represent the input gas flow rates to the first-stage dilution unit 31, the middle-stage dilution unit 32 and the last-stage dilution unit 33, and $q_{d1}$, $q_{d2}$ and $q_{d3}$ respectively represent the diluent gas flow rates in the first-stage dilution unit 31, the middle-stage dilution unit 32 and the last-stage dilution unit 33.

Thus, the flow rates of the diluent gas flowing through the diluent gas flow passages D1, D2 and D3 are respectively determined by following formulae (4) to (6), and the diluent gas control unit 71 applies the flow rates as target values to the respective flow rate control means MFC1, MFC2 and MFC3 so that the respective flow rate control means control the diluent gas flow rates to be equal to the target values.

$$q_{d1} = \qquad (4)$$
$$(1-R_{d1}) \cdot (q_{in2}+Q_{b1}) = (1-R_{d1}) \cdot \{R_{d2} \cdot R_{d3} \cdot (Q_{b2}+Q_{CPC})+Q_{b1}\}$$

$$q_{d2} = (1-R_{d2}) \cdot q_{in3} = (1-R_{d2}) \cdot R_{d3} \cdot (Q_{b2}+Q_{CPC}) \qquad (5)$$

$$q_{d3} = (1-R_{d3}) \cdot (Q_{b2}+Q_{CPC}) \qquad (6)$$

In addition, the flow rate $q_{ex}$ of the exhaust gas introduced from the exhaust gas introduction port PI at this time can be derived by following formula (7):

$$q_{ex} = R_{d1} \cdot \{R_{d2}R_{d2} \cdot (Q_{b2}+Q_{CPC})+Q_{b1}\} \qquad (7)$$

The following describes examples referring to specific numerical values.

It is assumed that, the flow rate of the constant flow rate instrument CFO1 is set to $Q_{b1}$=4.5 L/min, the flow rate of the constant flow rate instrument CFO2 is set to $Q_{b2}$=3.5 L/min, and the flow rate flowing through the particulate matters counting means CPC is set to $Q_{CPC}$=0.5 L/min, and the dilution ratios in the dilution units 31 to 33 are determined to be $R_{d1}$=1/10, $R_{d2}$=1/2 and $R_{d3}$=1/5, respectively.

Then, from the above formulae, the flow rates to be flowing in the respective diluent gas flow passages D1 to D3 in actual use are obtained as ($q_{d1}$=4.41 L/min, $q_{d2}$=0.4 L/min, and $q_{d3}$=3.2 L/min. Also, the introduction flow rate of the exhaust gas is obtained as $q_{ex}$=0.45 L/min, Moreover, in consideration of the above diluent gas flow rates in use, the flow rate control means MFC1 having a maximum flow rate of 5.5 L/min, flow rate control means MFC2 having a maximum flow rate of 1.0 L/min and flow rate control means MFC3 having a maximum flow rate of 5.5 L/min are used.

And in this embodiment, the characteristic measurement (calibration) prior to use of the respective constant flow rate instruments CFO1 and CFO2 is performed as follows.

First, the calibration pertaining to the constant flow rate instrument CFO1 of the first-stage dilution unit 31 is described.

First, for the constant flow rate instrument CFO1, the diluent gas having a flow rate equal to that of the gas flowing in use is introduced as a calibration gas.

Figure 5:
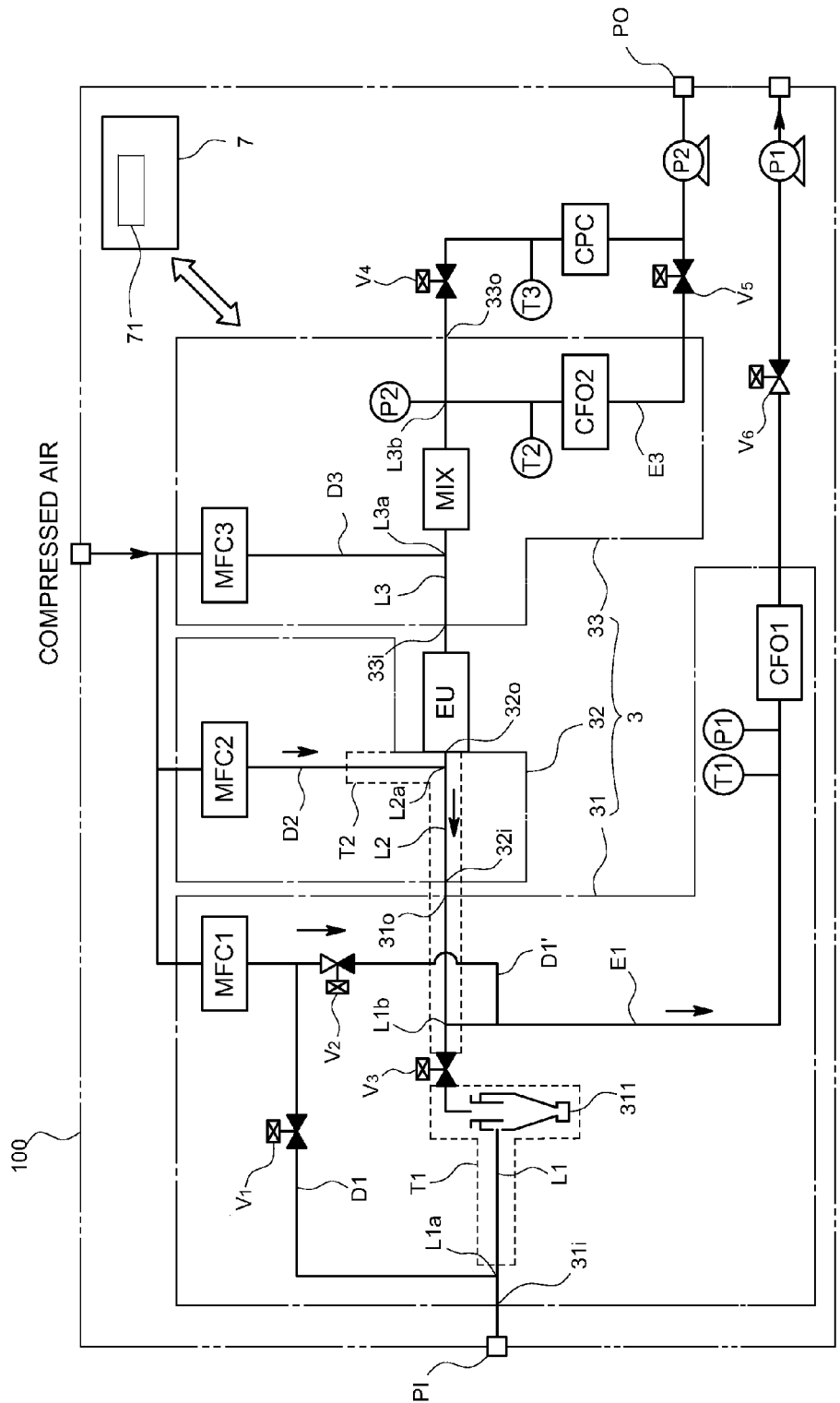
FIG. 5 is a fluid circuit diagram showing an internal structure of the gas analyzing system in the same embodiment and displaying a flow of the gas when calibrating a constant flow rate instrument CFO1 thereof.

Specifically, as shown in FIG. 5, the valves V1, V3, V4 and V5 are closed while the valves V2 and V6 are kept open, and the entire diluent gas only from and flowing through the diluent gas flow passage D1 of the first-stage dilution unit 31 and the diluent gas flow passage 132 of the middle-stage dilution unit 32 are rendered to flow into the constant flow rate instrument CFO1 of the first-stage dilution unit 31. Also, the temperature control mechanism T2 is adjusted so that the gas at a temperature substantially equal to that in use is rendered to flow into the constant flow rate instrument. CFO1.

At this time, the flow rate control means MFC1 is adjusted so that the gas of the same flow rate as that in use is rendered to flow into the diluent gas flow passage D1 of the first-stage dilution unit 31. In terms of numerical examples, the diluent gas flow rate is 4.41 L/min.

Then, a lacking flow rate 0.09 L/min insufficient to the predetermined flow rate 4.5 L; min of the constant flow rate instrument CFO1 which is regarded as an input gas is fed from the diluent gas flow passage D2 of the middle-stage dilution unit 32 as an alternative input gas to the first-stage dilution unit 31.

Then, the upstream side pressure and temperature of the constant flow rate instrument CFO1 under this condition are measured by the pressure sensor P1 and the temperature sensor T1, and the measurement values are substituted into, e.g., Formula (A) mentioned above so as to specify the sonic conductance C of the constant flow rate instrument CFO1.

Next, the calibration of the constant flow rate instrument CFO2 of the last-stage dilution unit 33 is described.

Figure 6:
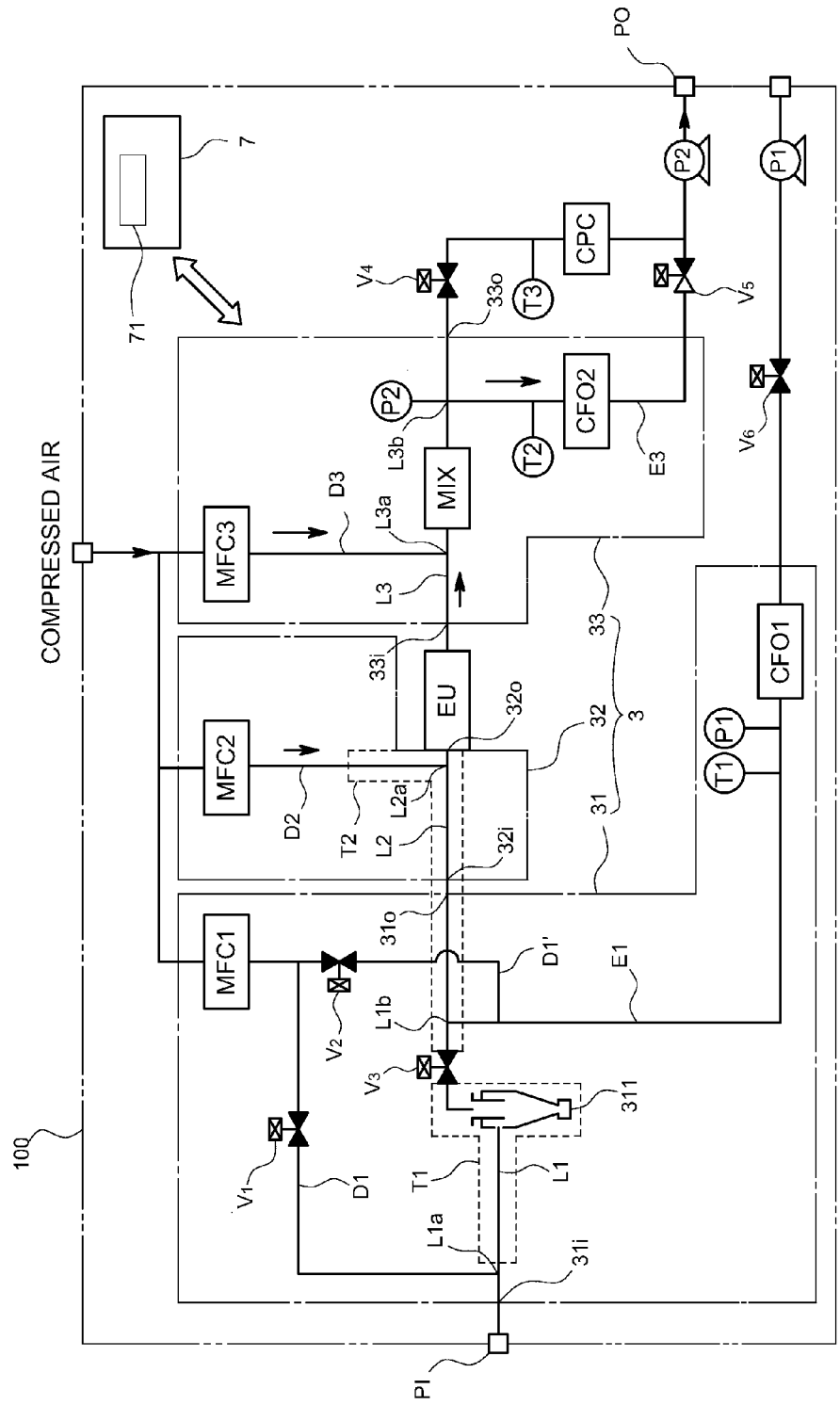
FIG. 6 is a fluid circuit diagram showing an internal structure of the gas analyzing system in the same embodiment and displaying a flow of the gas when calibrating a constant flow rate instrument CFO2 thereof.

As shown in FIG. 6, the valves V1, V2, V3, V4 and V6 are closed while the valve V5 is kept open, and the entire diluent gas only from and flowing through the diluent gas flow passage D3 of the last-stage dilution unit 33 and the diluent gas flow passage D2 of the middle-stage dilution unit 32 are rendered to flow into the constant flow rate instrument CFO2 of the last-stage dilution unit 33. Also, the evaporator unit EU is operated and the temperature control mechanism T2 is adjusted so that the gas at a temperature substantially equal to that in use is rendered to flow into the constant flow rate instrument CFO2.

At this time, the flow rate control means MFC3 is adjusted so that the gas of the same flow rate as that in use is rendered to flow into the diluent gas flow passage D3 of the last-stage dilution unit 33. In terms of the numerical examples, the diluent gas flow rate is 3.2 L/min. Then, a lacking flow rate 0.3 L/min insufficient to the predetermined flow rate 3.5 L/min of the constant flow rate instrument CFO2 which is regarded as an input gas is fed from the diluent gas flow passage D2 of the middle-stage dilution unit 32 as an alternative input gas of the last-stage dilution unit 33, Then, the upstream side pressure and temperature of the constant flow rate instrument CFO2 under this condition are measured by the pressure sensor P2 and the temperature sensor T2, and the measurement values are substituted into, e.g., Formula (A) so as to specify the sonic conductance C of the constant flow rate instrument CFO2.

In addition, each of the operations pertaining to the calibrations mentioned above such as, e.g., opening and closing of the valves V1 to V6, controls of the flow rate control means MFC1 to MFC3, measuring of the pressure and temperature and calculation/storing of the sonic conductance C is all automatically performed by, the information processing device 7 and the operator is merely required to input instructions of performing a calibration. Of course, the setting or calibration may be manually performed in sequence by an operator.

Figure 7:
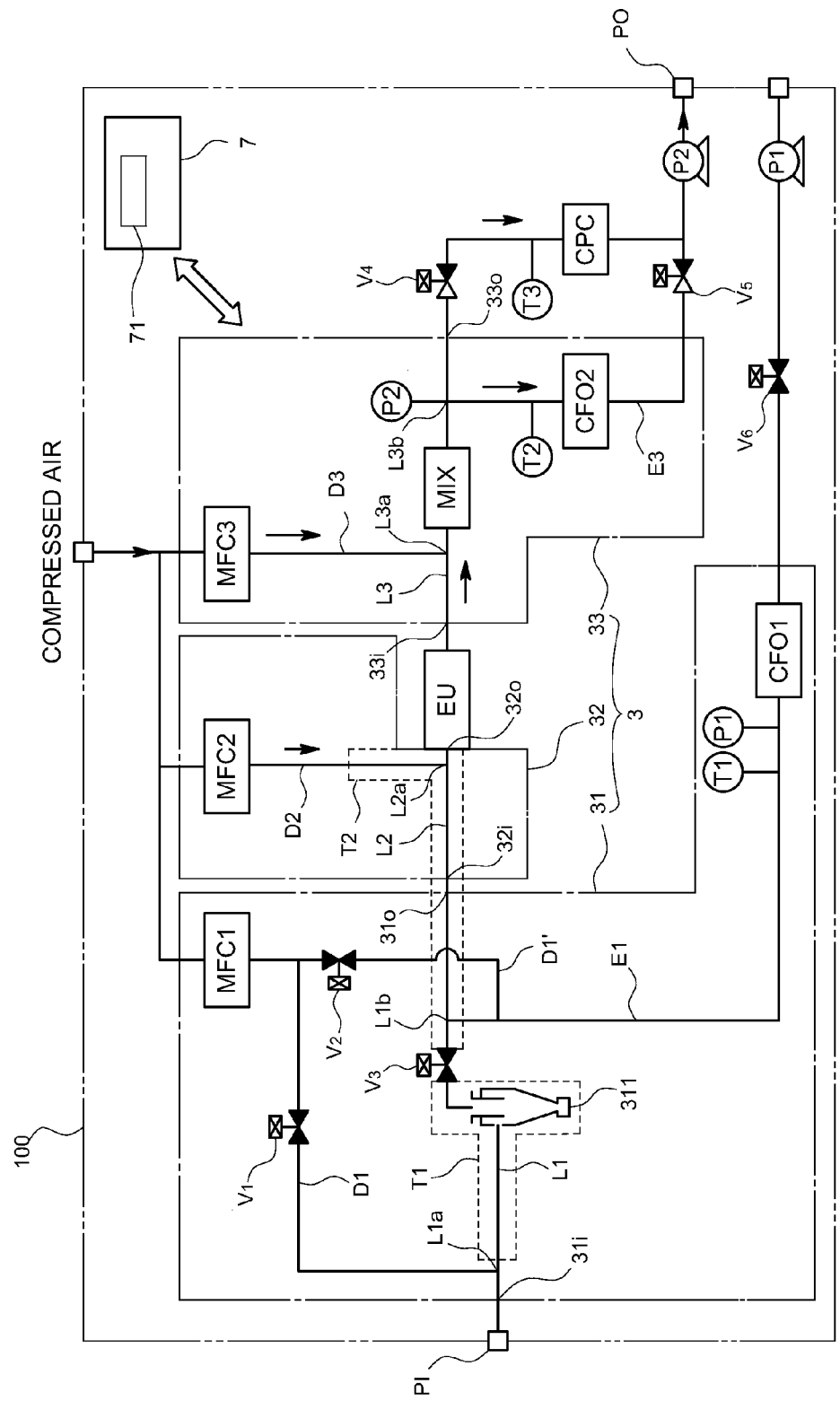
FIG. 7 is a fluid circuit diagram showing an internal structure of the gas analyzing system in the same embodiment and displaying a flow of the gas when calibrating particulate matters counting means.

Further, in the present embodiment, it flow rate calibration of the particulate matters counting means CPC is also performed. At this time, as shown in FIG. 7, the valves V1, V2, V3 and V6 are closed while the valves V4 and V5 are kept open, and the entire diluent gas only from and flowing through the diluent gas flow passage D3 of the last-stage dilution unit 33 and the diluent gas flow passage D2 of the middle-stage dilution unit 32 are rendered to flow into the constant flow rate instrument CFO2 and the slit A3 of the particulate matters counting means CPC. Also, the evaporator unit EU is operated and the temperature control mechanism T2 is adjusted so that the temperature of the gas is kept to be substantially equal to that in use.

Since the calibration of the constant flow rate instrument CFO2 has been already finished, the diluent gas of 3.5 L/min flows here. Meanwhile, since the diluent gas of 0.5 L/min equal to the flow rate in use is rendered to flow into the particulate matters counting means CPC, the diluent gas of 3.2 L/min equal to the flow rate in use is rendered to flow from the diluent gas flow passage D3 of the last-stage dilution unit 33 and a lacking flow rate 0.8 L/min which is regarded as an input gas is fed from the diluent gas flow passage D2 of the middle-stage dilution unit 32.

Then, the upstream side pressure and temperature of the particulate matters counting means CPC under this condition are measured by the pressure sensor P2 and the temperature sensor T3, and the measurement values are substituted into, e.g., Formula (A) mentioned above so as to specify the sonic conductance C of the particulate matters counting means CPC.

Thus, with this configuration, when performing a calibration, since the diluent gas for the corresponding one dilution unit is rendered to flow by a flow rate equal to that in use with the diluent inflow gas from the other dilution unit used as simulation input gas so that the operating points of the flow rate control means regarding the diluent gas both in use and in calibration are made coincident with each other, the error in adjusting the flow rate by the flow rate control means can be reduced. Such an aspect of the embodiment is particularly effective in the case of frequently performing the calibrations, In addition, in the present embodiment, since a dilution unit adjacent to one calibration-target dilution unit is used as the other dilution unit, the passage of the input gas can be made closer to the condition in use so that there can be obtained an effect that the temperature can be easily adjusted equally both in use and in calibration.

It is noted that the present invention is not limited to the embodiments described above.

For example, in the embodiment described above, although the diluent gas flow rate in one calibration-target dilution unit is made equal to that in use, the dilution ratio may be made equal to that in use. Referring to a calibration pertaining to the constant flow rate instrument CFO1 as a specific example, since the set dilution ratio Rd1 in the first-stage dilution unit 31 is 1/10 and the set flow rate of the constant flow rate instrument CFO1 is 4.5 L/min, the diluent gas of a flow rate of 4.05 L/min which is 9/10 of 4.5 L/min is rendered to flow in the flow rate control means MFC1 of the diluent gas flow passage D1 and the lacking flow rate of 0.45 L/min is supplemented with the diluent gas of the middle-stage diluent unit 32 fed as the input gas. Thus, the dilution ratios of the input gas and the diluent gas in the first-stage dilution unit 31 can be made equal to those in use.

With this configuration, since the dilution ratio in use can be coincident with that in calibration, there can be obtained the same effect as described above. Also, it becomes efficient in the case where the dilution ratio is frequently changed in comparison to the first aspect of the present invention. In addition, if the dilution ratio is made smaller and smaller, this aspect will be ultimately identical to the embodiment mentioned above.

Moreover, although the introduced diluent gas as the simulation input gas may be derived from any one or more other dilution units, it is more preferable in terms of the accuracy to use the diluent gas of the other flow rate control means having a flow rate control range close to the flow rate of the input gas. Therefore, according to the setting of the dilution ratio, the other dilution unit for use in calibration may be altered.

Further, two dilution units maybe used and four may be used. The dilution mechanism can he applied other systems than a gas analyzing system.

The ingredient analyzing means is not limited to the particulate matters counting means. The ingredient analyzing means may be an ingredient analyzing apparatus for exhaust-gas from an internal combustion engine such as a non-dispersed infrared absorption technique analyzing means (NDIR), a flame ionization detector (FID), or a chemiluminescence detector (CLD). In these cases, by arranging a measuring or controlling mechanism such as a critical orifice type constant flow rate instrument, a mass flow meter, a mass flow controller, or capillary, it can be achieved to measure or control gas flow rate more accurate in the gas analyzing system.

In addition, the present invention is not limited to the above embodiments, and it is needless to say that various changes and modifications can be made within the scope of the present invention unless departing from the spirit thereof.

INDUSTRIAL APPLICABILITY

According to the present invention, the condition at the time of measuring the characteristics of the critical orifice type constant flow rate instrument is brought near to the condition in actual use as close as possible so as to be able to reduce the error of the dilution ratio.

REFERENCE SIGNS LIST

100 . . . Gas analyzing system
3 . . . Dilution mechanism
31, 32, 33 . . . Dilution unit
31i, 32i, 33i . . . Input terminal
31o, 32o, 33o . . . Output terminal
L1, L2, L3 . . . Main flow passage
L1a, L2a, L3a . . . Confluence
L1b, L3b . . . Branch point
D1, D2, D3 . . . Diluent gas flow passage
E1, E3 . . . Derivation flow passage
MFC1, MFC2, MFC3 . . . Flow rate control means
CFO1, CFO2 . . . Critical orifice type constant flow rate instrument

The invention claimed is:

1. A method of measuring characteristics of a critical orifice type constant flow rate instrument applied to a dilution mechanism constructed in a manner that each of a plurality of dilution units is constructed such that a confluence is provided at an intermediate portion of a main flow passage connecting between an input terminal and an output terminal for leading input gas and a diluent gas flow passage provided with a flow rate controller is connected to the confluence so that diluent gas of a prescribed flow rate having a predetermined dilution ratio is introduced to the main flow passage and the plurality of dilution units are connected in series and at least one of the dilution units is provided with a branch point at the intermediate portion of the main flow passage so that a derivation flow passage provided with the critical orifice type constant flow rate instrument is connected to the branch point so as to derive the gas of a constant flow rate from the main flow passage, the method comprising:
based on selective operation of a valving arrangement of the dilution mechanism, flowing the diluent gas from the diluent gas flow passage in the corresponding one dilution unit and the diluent gas from the diluent gas flow passages in one or more other dilution units to a derivation flow passage of one of the dilution units such that the total flow rate thereof is equal to the constant flow rate and that the flow rate of the diluent gas from the corresponding one dilution unit is equal to the prescribed flow rate; and
measuring the flow rate characteristics of the corresponding critical orifice type constant flow rate instrument based on at least an upstream side pressure of the critical orifice type constant flow rate instrument in the corresponding derivation flow passage at this time.

2. A method of measuring characteristics of a critical orifice type constant flow rate instrument applied to a dilution mechanism constructed in a manner that each of a plurality of dilution units is constructed such that a confluence is provided at an intermediate portion of a main flow passage connecting between an input terminal and an output terminal for leading input gas and a diluent gas flow passage provided with a flow rate controller is connected to the confluence so that diluent gas of a prescribed flow rate having a predetermined dilution ratio is introduced to the main flow passage and the plurality of dilution units are connected in series and at least one of the dilution units is provided with a branch point at the intermediate portion of the main flow passage so that a derivation flow passage provided with the critical orifice type constant flow rate instrument is connected to the branch point so as to derive the gas of a constant flow rate from the main flow passage, the method comprising:

based on selective operation of a valving arrangement of the dilution mechanism, flowing the diluent gas from the diluent gas flow passage in the corresponding one dilution unit and the diluent gas from the diluent gas flow passages in one or more other dilution units to a derivation flow passage of one of the dilution units such that the total flow rate thereof is equal to the constant flow rate and that a dilution ratio of the flow rate of the diluent gas from the one or more other dilution units to the flow rate of the diluent gas from the corresponding one dilution unit is equal to the predetermined dilution ratio; and measuring the flow rate characteristics of the corresponding critical orifice type constant flow rate instrument based on at least an upstream side pressure of the critical orifice type constant flow rate instrument in the corresponding derivation flow passage at this time.

3. The method of measuring the characteristics of the constant flow rate instrument according to claim 1, wherein the one or more other dilution units are upstream side or downstream side dilution units adjacent to the corresponding one dilution unit.

4. The method of measuring the characteristics of the constant flow rate instrument according to claim 2, wherein the one or more other dilution units are upstream side or downstream side dilution units adjacent to the corresponding one dilution unit.

5. A dilution mechanism comprising:

a plurality of dilution units each constructed such that a confluence is provided at an intermediate portion of a main flow passage connecting between an input terminal and an output terminal for leading input gas and a diluent gas flow passage provided with a flow rate controller is connected to the confluence so that diluent gas of a prescribed flow rate having a predetermined dilution ratio is introduced to the main flow passage and the plurality of dilution units are connected in series and at least one of the dilution units is provided with a branch point at the intermediate portion of the main flow passage so that a derivation flow passage provided with a critical orifice type constant flow rate instrument is connected to the branch point so as to derive the gas of a constant flow rate from the main flow passage, wherein the dilution mechanism further includes an information processing device programmed to control selective operation of a valving arrangement of the dilution mechanism such that only the diluent gas from the diluent gas flow passage in the corresponding one dilution unit and the diluent gas from the diluent gas flow passages in one or more other dilution units flow into the derivation flow passage of one of the dilution units, and the flow rate controllers such that the total flow rate of the respective diluent gas at this time is equal to the constant flow rate and that the flow rate of the diluent gas from the corresponding one dilution unit is equal to the prescribed flow rate, and measuring the flow rate characteristics of the corresponding critical orifice type constant flow rate instrument based on at least an upstream side pressure of the critical orifice type constant flow rate instrument in the corresponding derivation flow passage.

6. A dilution mechanism comprising:

a plurality of dilution units each constructed such that a confluence is provided at an intermediate portion of a main flow passage connecting between an input terminal and an output terminal for leading input gas and a diluent gas flow passage provided with a flow rate controller is connected to the confluence so that diluent gas of a prescribed flow rate having a predetermined dilution ratio is introduced to the main flow passage and the plurality of dilution units are connected in series and at least one of the dilution units is provided with a branch point at the intermediate portion of the main flow passage so that a derivation flow passage provided with a critical orifice type constant flow rate instrument is connected to the branch point so as to derive the gas of a constant flow rate from the main flow passage, wherein the dilution mechanism further includes an information processing device programmed to control a selective operation of a valving arrangement of the dilution mechanism such that only the diluent gas from the diluent gas flow passage in the corresponding one dilution unit and the diluent gas from the diluent gas flow passages in one or more other dilution units flow into the derivation flow passage of one of the dilution units, and the flow rate controllers such that the total flow rate of the respective diluent gas at this time is equal to the constant flow rate and that the dilution ratio of the flow rate of the diluent gas from the one or more other dilution units to the flow rate of the diluent gas from the corresponding one dilution unit is equal to the predetermined dilution ratio, and measuring the flow rate characteristics of the corresponding critical orifice type constant flow rate instrument based on at least an upstream side pressure of the critical orifice type constant flow rate instrument in the corresponding derivation flow passage.

7. A gas analyzing system including the dilution mechanism according to claim 6 further comprising an ingredient analyzer adapted to analyze ingredients of exhaust gas of an internal combustion engine introduced to a first-stage dilution unit and derived from a last-stage dilution unit.

8. The gas analyzing system according to claim 7, wherein the ingredient analyzer comprises a second critical orifice type constant flow rate instrument inside thereof and is constructed such that only the diluent gas from the dilution unit is flowable into the ingredient analyzer by a prescribed flow rate, and wherein the information processing device measures the flow rate characteristics of the ingredient analyzer based on at least an upstream side pressure of the ingredient analyzer at this time.

9. The gas analyzing system according to claim 7, wherein the ingredient analyzer is a particulate matters counter counting particulate matters contained in the exhaust gas.

10. The gas analyzing system according to claim 8, wherein the ingredient analyzer is a particulate matters counter counting particulate matters contained in the exhaust gas.

\* \* \* \* \*